United States Patent
Utterberg

[11] Patent Number: 5,951,529
[45] Date of Patent: *Sep. 14, 1999

[54] NEEDLE PROTECTOR SHEATH

[75] Inventor: David S. Utterberg, Seattle, Wash.

[73] Assignee: Medisystems Technology Corporation, Las Vegas, Nev.

[*] Notice: This patent is subject to a terminal disclaimer.

[21] Appl. No.: 08/662,685

[22] Filed: Jun. 13, 1996

Related U.S. Application Data

[60] Division of application No. 08/420,700, Apr. 11, 1995, Pat. No. 5,562,637, which is a continuation-in-part of application No. 08/275,880, Jul. 15, 1994, Pat. No. 5,562,636.

[51] Int. Cl.$^6$ ........................................................ A61M 5/00
[52] U.S. Cl. ........................... 604/263; 604/171; 604/177; 604/198
[58] Field of Search ...................................... 604/192, 198, 604/263, 177, 163, 171, 110, 174, 162, 197; 128/919

[56] References Cited

U.S. PATENT DOCUMENTS

| | | |
|---|---|---|
| 4,917,669 | 4/1990 | Bonaldo . |
| 4,941,881 | 7/1990 | Masters et al. . |
| 4,946,447 | 8/1990 | Hardcastle et al. . |
| 4,994,046 | 2/1991 | Wesson et al. . |
| 5,092,461 | 3/1992 | Adam . |
| 5,112,311 | 5/1992 | Utterberg et al. . |
| 5,120,320 | 6/1992 | Fayngold . |
| 5,171,231 | 12/1992 | Heiliger . |
| 5,219,339 | 6/1993 | Saito . |
| 5,290,264 | 3/1994 | Utterberg . |
| 5,330,438 | 7/1994 | Gollobin et al. . |
| 5,350,368 | 9/1994 | Shields . |
| 5,562,636 | 10/1996 | Utterberg ................................ 604/198 |
| 5,562,637 | 10/1996 | Utterberg ................................ 604/198 |
| 5,704,924 | 1/1998 | Utterberg et al. ....................... 604/263 |
| 5,772,638 | 6/1998 | Utterberg et al. ....................... 604/263 |
| 5,827,239 | 10/1998 | Dillon et al. . |

FOREIGN PATENT DOCUMENTS

| | | |
|---|---|---|
| 651308 | 7/1994 | Australia . |
| 0265159 | 4/1988 | European Pat. Off. . |
| 0353916 | 2/1990 | European Pat. Off. . |
| 0459953 | 12/1991 | European Pat. Off. . |
| 1-212561 | 8/1989 | Japan . |
| 95/24232 | 9/1995 | WIPO . |

*Primary Examiner*—Ronald Stright
*Attorney, Agent, or Firm*—Gerstman, Ellis & McMillin, Ltd.

[57] ABSTRACT

A needle protector sheath comprises a body having a top wall, sidewalls and open ends. A slot is formed in each sidewall to slidingly receive a needle wing extending through each of the slots. Typically the slots extend through one end of the protector sheath. The protector sheath also defines an open, bottom aperture extending from end to end of the body, to permit the sheath to be laterally applied to tubing connected to a winged needle and to be advanced to a position where the needle tip is recessed in the sheath and the needle wings extend through the slots. In another embodiment an elongated anchor member may extend forwardly from the body to be manually pressed to retain the protector sheath as the needle is being withdrawn from the skin of a patient. The anchor member may have an outer end portion that bends away from the patient in position of use. Also, a novel sheath design and slot arrangement is disclosed.

24 Claims, 4 Drawing Sheets

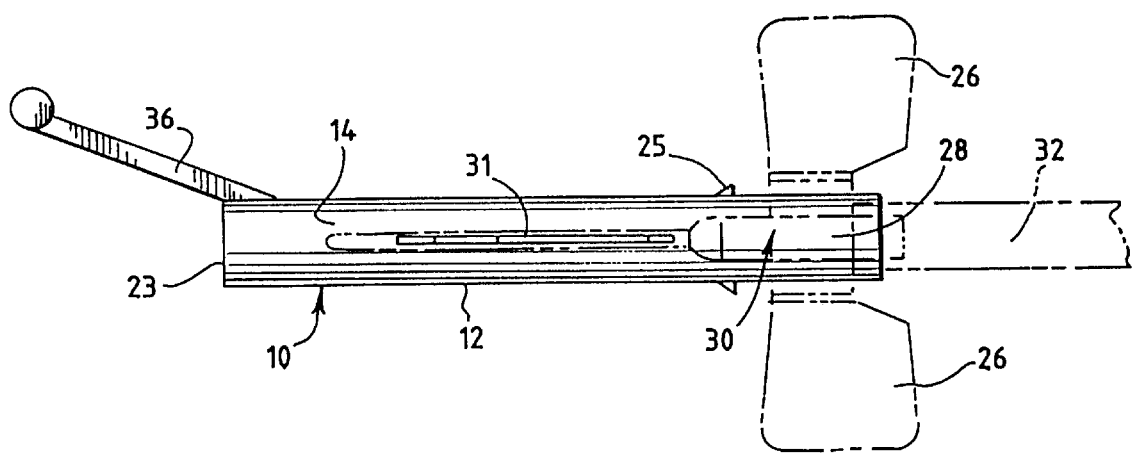
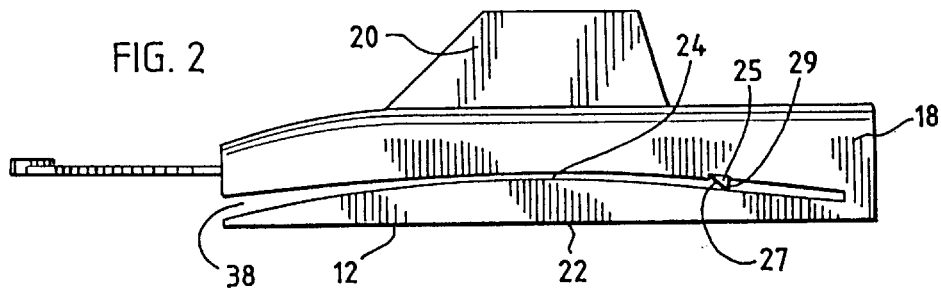
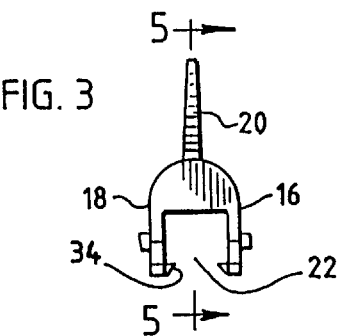
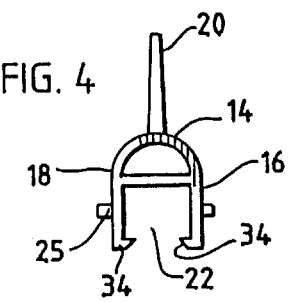
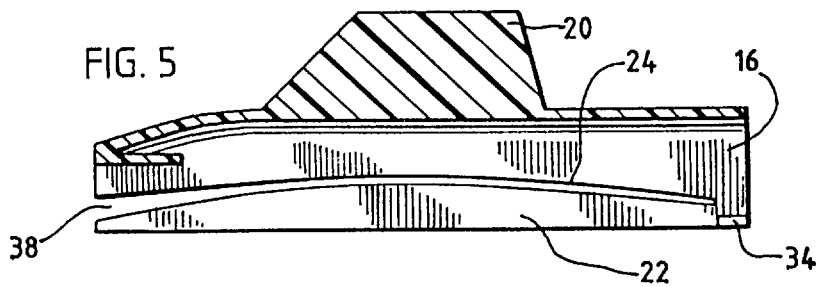

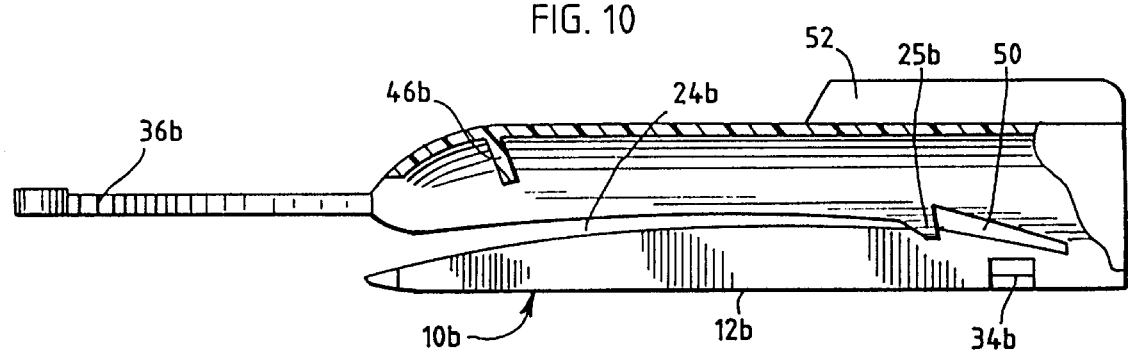
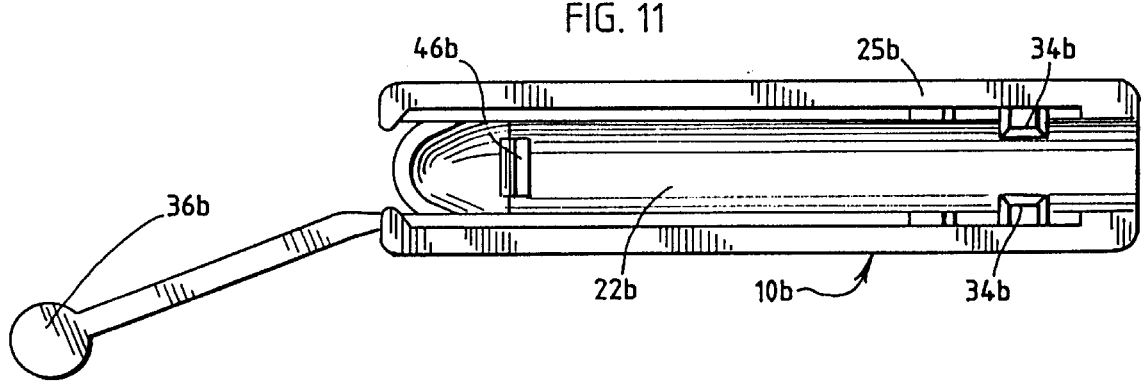
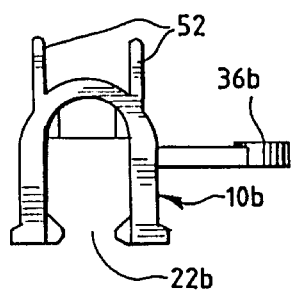

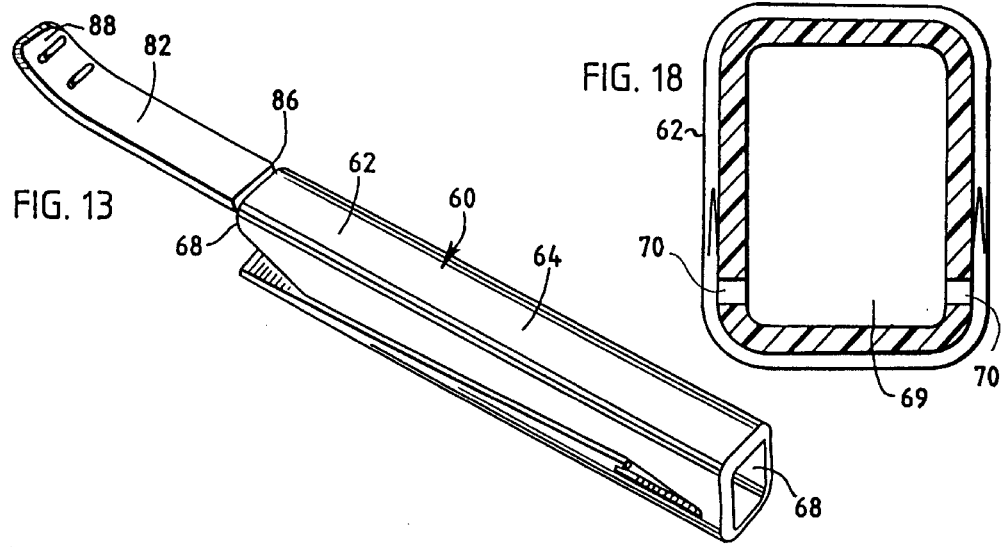
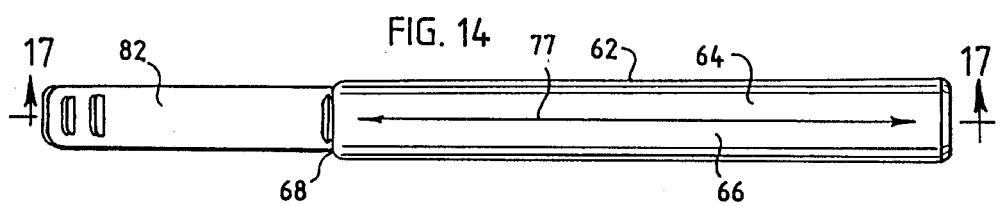
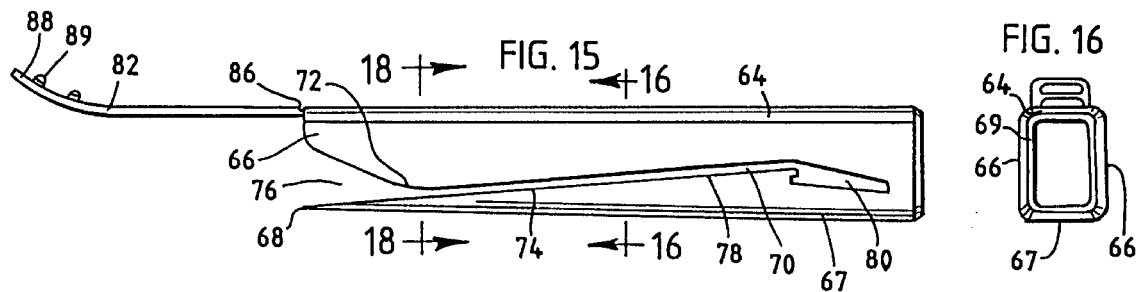
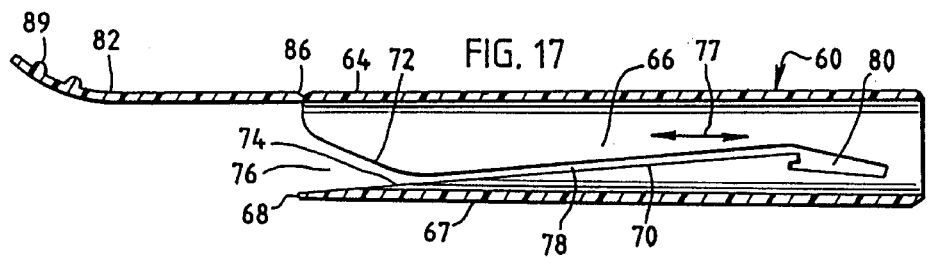

NEEDLE PROTECTOR SHEATH

CROSS REFERENCE TO RELATED APPLICATION

This is a division of U.S. patent application Ser. No. 08/420,700, filed Apr. 11, 1995, now U.S. Pat. No. 5,562,637, which, in turn, is a continuation-in-part of U.S. patent application Ser. No. 08/275,880, filed on Jul. 15, 1994, now U.S. Pat. No. 5,562,636.

BACKGROUND OF THE INVENTION

Utterberg et al. U.S. Pat. No. 5,112,311 discloses a sliding body or sheath which is carried on a tubular set such as a fistula set for hemodialysis, having a winged needle at the end. There is a significant need to provide the maximum amount of protection to medical personnel against needle sticks, especially with respect to needles that are used in contact with blood. The sliding sheath of the cited patent can be brought forward to enclose the needle as the needle is retracted from the patient, so that the needle is immediately secured against accidental needle sticks by the sliding device. The wings of the needle, which are commonly used in conjunction with a variety of intravenous needles, slide within opposed slots of the needle protector of the cited patent, and are locked in place when the needle is fully withdrawn into the sliding sheath as described.

By this present invention, improvements are provided to the device disclosed in the above-cited patent. Specifically, the device of the prior art is typically placed on a needle set prior to use and the wings engaged in the slots. Even when the sliding sheath is retracted away from the needle as much as possible, medical personnel have found its presence to be inconvenient during the process of venipuncture and taping of the needle wings to the skin of the patient.

Also, by this invention, improvements in functioning are achieved by a modification of the shape of the slots of the sliding sheath or body through which the needle wings penetrate. Particularly, withdrawal of the needle from the patient can be facilitated in an axial movement, reducing the potential for the point to cause a hematoma. Also, advancement of the sheath about the needle is facilitated.

Thus, significantly improved needle protector sheaths are provided, some of which can be applied to a needle and attached tubing after the needle has been inserted into the vein of a patient. Additionally, other improvements over the prior art are found herein.

DESCRIPTION OF THE INVENTION

In accordance with this invention, a needle protector sheath is provided which comprises a body having a top wall, side walls, and at least partially open ends. A slot is formed in at least one of the walls, and preferably in each side wall, to slidingly receive a needle wing extending through each of the slots. The protector sheath may define an open, bottom aperture extending from end to end of the body to permit the sheath to be laterally applied to tubing connected to a winged needle. After such lateral application, the sheath or body can be advanced in sliding manner along the tubing to a position where the needle tip becomes recessed in the sheath, and the needle wing or wings extend through the slot or slots present. Thus some types of the sheath of this invention can be mounted on a needle set after the needle has been placed in a vein or a fistula.

Detents may be provided on the side walls adjacent the bottom aperture to help retain a winged needle, and its connected tubing, within the body of the protector sheath. The bottom aperture is proportioned to permit a needle, needle hub or its connected tubing to be inserted through the bottom aperture for laterally installing the protector sheath onto the tubing of the neeedle set.

The body of the protector sheath may further define a needle tip retaining wall which is typically formed between the top and side walls adjacent to one end of the body. Such a retaining wall may be positioned substantially parallel to the longitudinal axis of the body to define a closed pocket with the remainder of the body, for receiving a pointed needle tip which is carried within the protector sheath. This provides an added, desired sequestering of the needle tip for improved safety. Alternatively, the retaining wall may be positioned at an acute angle, for example about 30° to 60° to the longitudinal axis of the body, which also defines a closed pocket with the remainder of the body for needle tip retention. If desired, the retaining wall may be essentially perpendicular to the longitudinal axis of the body (or in fact, it may be a partial front wall) to form a barrier wall against which the needle tip may impinge, for further protection against accidental needle sticks.

It also is desirable for the slots of the protector sheath body to extend toward the sheath bottom as they extend toward an open slot end at one end of the body. This has been found to facilitate the easy withdrawal of a needle emplaced in the venous system of a patient, with the needle tip directed in the direction of the one end of the body. As the needle is withdrawn, the needle protector can receive the needle wings in the slots. Because of the curve of the slots toward the bottom of the body, the needle wings are more easily received and engaged by the slots as the needle is withdrawn, with the needle protector sheath being held stationary, so that the needle may be withdrawn rearwardly into the needle protector sheath. The slots preferably extend through one end of the body at the slot end nearest the bottom aperture.

As another aspect of the inventions disclosed herein, an elongated anchor member can extend forwardly from the body to be manually pressed to retain the protector sheath as the needle is being withdrawn from the skin of a patient, as broadly disclosed in the cited U.S. Pat. No. 5,112,311. By this invention, the anchor member may have a straight, major portion comprising most of the length of said anchor member. Also, the anchor member may define an outer end portion that bends away from the patient in position of use, typically as a curved shape rather like the tip of a ski. Thus, when the sheath of this invention is being advanced toward a position to receive the needle when the needle is to be withdrawn from the patient, the anchor member more easily slides over adjacent bandages and the like.

Preferably, the anchor also comprises a substantially flat, sheath-like extension of the top wall. Also, the anchor may join the top wall at a junction line which is defined by a line of bending weakness, to facilitate its downward bending when manually pressed.

The body of the protector sheath, which may be rectangular in cross-section, is preferably tapered by about 0.2 to 5 degrees to define a forward end of the body that is of less cross-sectional dimension than a rear end of the body. This small amount of tapering or "draft" facilitates the molding of the sheath.

It is also a preferred embodiment for the slots to extend through a forward end of the body with the slots each defining upper and lower surfaces. A major portion of the slots preferably defines an acute angle to the longitudinal axis of the needle protector sheath so that most of the extent of the slots extends in such an acute angular relationship. Forward portions of the slots slope toward the top wall of the sheath as they extend toward the rear sheath end so that a needle is not bent or twisted as the sheath is advanced because of the acute angle of that forward slot portion. The rear portions of the slots may slope away from the top wall as they extend toward the rear end, to tip the point of the needle and hub having wings carried in the rear slot portions toward the top wall.

Forward end portions of the lower slot surfaces preferably extend at an acute angle to the longitudinal axis of the body to intersect the forward body end at a position that is substantially maximally spaced from the top wall. In those circumstances where a bottom wall is present, the lower slot surfaces preferably merge with the inner surface of a forward end portion of the bottom wall, to achieve such maximal spacing. The forward end portions of the upper slot surfaces may diverge from the lower slot surfaces and extend toward the top wall. Thus, wide slot portions are provided in each sidewall at the forward body end, which slot portions taper inwardly to communicate with the remainder of the slots, which remaining portions are substantially narrower. Thus, it becomes easy to advance the sliding sheath so that the front end thereof engages and captures the projecting wings of a needle hub, with the wings projecting outwardly through the slots.

Preferably, a major portion of each of the slots defines an acute angle to the longitudinal axis. Also, most of the length of the slots may be straight.

Thus, needle protector sheaths are provided which exhibit significant improvements in structure and functioning over those of the prior art.

The terms "top", "bottom", and "side" as used herein are relative and exemplary in intent, and are not intended to exclude the use of a protector sheath of this invention in a different or varying position of spatial orientation.

DESCRIPTION OF THE DRAWINGS

Referring to the drawings, FIG. 1 is a plan view of one embodiment of the sheath of this invention, shown carrying a winged needle in retracted relation so that the sheath is surrounding the needle tip;

FIG. 2 is an elevational view of the sheath of FIG. 1;

FIGS. 3 and 4 are, respectively, front and rear views of the sheath of FIG. 1, with the winged needle not being shown;

FIG. 5 is a longitudinal, sectional view of the sheath, with the "anchor" deleted;

FIG. 10 a longitudinal, sectional view of another embodiment of the sheath of this invention;

FIG. 11 is bottom, plan view of the sheath of FIG. 10;

FIG. 12 is proximal end view of the sheath of FIG. 10;

FIG. 13 is a perspective view of another embodiment of the sheath of this invention;

FIG. 14 is a top plan view of the sheath of FIG. 13;

FIG. 15 is an elevational view of the sheath of FIG. 13;

FIG. 16 is a transverse sectional view taken along line 16—16 of FIG. 15;

FIG. 17 is a longitudinal sectional view taken along line 17—17 of FIG. 14; and

FIG. 18 is an enlarged, transverse sectional view taken along line 18—18 of FIG. 15.

DESCRIPTION OF SPECIFIC EMBODIMENTS

Figure 6:
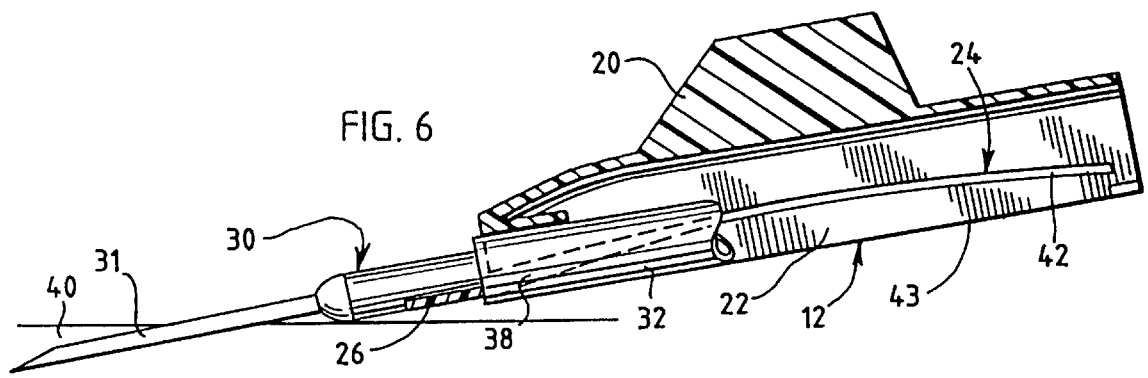
FIG. 6 is a longitudinal, sectional view of another sheath embodiment, showing the interrelationship of the sheath with a winged needle as the sheath is being advanced forwardly about the needle.

Referring to FIGS. 1 through 8, a needle protector sheath 10 is disclosed, being generally similar in structure and function to the needle sheaths shown in U.S. Pat. No. 5,112,311 except as otherwise described herein. Sheath 10 comprises a body 12 which has a top wall 14 and side walls 16, 18, plus an optional gripping rib 20, integral with top wall 14, to facilitate manual gripping of the protector sheath. Apart from the presence of gripping rib 20, body 12 is shown by FIGS. 3 and 4 to be of generally U-shaped or C-shaped cross-section, defining an open bottom aperture 22 which extends from end to end of body 12.

Sheath 10 also defines a pair of slots 24, each slot 24 being defined in a separate side wall 16, 18, with each slot 24 extending through an end 23 of body 12. The purpose of slots 24 is to receive therethrough the wings 26 of a winged needle hub 28 projecting therethrough which, in conjunction with needle 31, is generally referred to herein as a "winged needle" 30. The winged needle 30 is shown to be connected to flexible tubing 32 of a fistula set used in hemodialysis, for example.

In the cited prior art patent, the needle protector sheath shown therein may be mounted upon tubing of a fistula set or the like from the needle or tube end of the set, to enclose completely the needle and/or hub with at least one end of the guard. It is then advanced distally to enclose the needle as the needle is being withdrawn from the patient. Specifically, the prior art protector sheath can be mounted on the winged needle of a set by passing the needle through the proximal end of the needle protector sheath, and then moving the sheath rearwardly out of the way of the needle, with the wings sliding into and along the slots of the protector sheath.

Locking detents 25 are provided with a distally facing angled surface 27 and a proximally facing perpendicular surface 29, so as to provide snap fit retention for the wings sliding in slots 24 after the winged needle 30 has entered into fully enclosed relationship with protector sheath 10, as shown in FIG. 1, for the substantially permanent enclosing of the needle in the sheath.

As an advantage, the protector sheath of this invention is capable of being mounted on the tubing 32 of a fistula set from the side, even after the needle has been positioned in the vascular system of a patient, without the need for access to an end of the set. Instead, one can simply place the protector sheath laterally about tubing 32, with the tubing being retained to an extent by detents 34. Then, the protector sheath may slide forwardly relative to the needle as the needle is withdrawn, so that the needle becomes immediately enclosed by the protector sheath. This can be accomplished, as taught in the previously cited patent, by pressing a finger against projecting anchor 36, which may be an integral part of protector sheath 10, so that as the needle is withdrawn, the protector sheath is held in stationary position, causing the needle to retract into the sheath.

Figure 7:
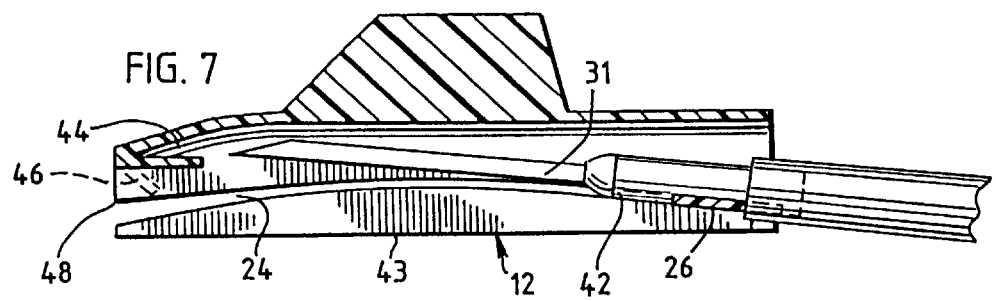
FIG. 7 is a longitudinal, sectional view showing the needle inside of the sheath of FIG. 6 in a position substantially corresponding to the position of FIG. 1.
Figure 8:
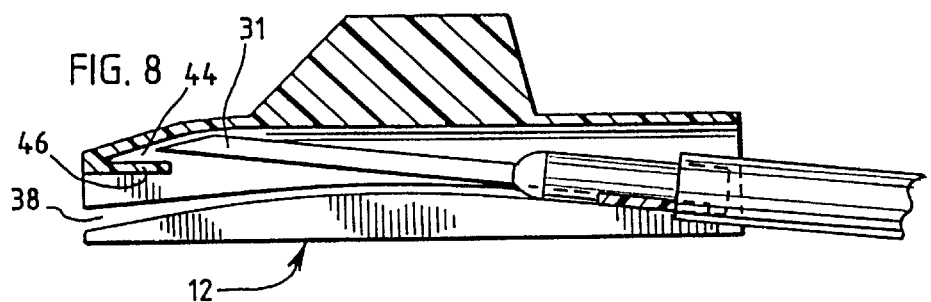
FIG. 8 is a longitudinal, sectional view of the sheath of FIG. 7, showing how the needle enclosed in the sheath can be advanced so that its point is inserted into an internal pocket of the sheath.

Because slots 24 may have a downward curve at their forward portions 38, it becomes easier for the forward open slot portions 38 to each engage a respective wing 26 as the winged needle 30 and body 12 are brought together, as implied by the different needle positions of FIGS. 6 and 7. Body 12 is of identical design to that of the previous embodiment except for the deletion of anchor 36. Thus, the proximity of the forward end 38 of each slit 24 to the lower edge of body 12 facilitates convenient engagement of the needle wings for withdrawal of the needle without excessive movement of needle 31 in the tissue 40 of the patient. Hence, the protector sheath of this invention can be applied to a needle which is being withdrawn with less patient discomfort. Also, forward slot ends 38 may be outwardly flared to more easily engage and receive the respective wings 26.

It can also be seen that slot 24 has a rear or proximal end 42 which also exhibits a slope toward the bottom edge 43 of body 12. The effect of this slope is to cause needle 31 to tilt upwardly as shown in FIG. 7. Then, body 12 can be retracted again relative to needle 31 to cause needle 31 to reside in the pocket 44 which is defined by needle tip retaining wall 46, as particularly shown in FIG. 8.

Needle tip retaining wall 46 is shown to be positioned substantially parallel to the longitudinal axis of body 12, to define a closed pocket 44 with the remainder of the body, for retention of the pointed tip of needle 31. Alternatively if desired, retaining wall 46 may extend at about a 45° angle to the axis of body 12, as shown in dotted lines in FIG. 7 to provide a more open pocket 44. Also if desired, retaining wall 46 may be substantially perpendicular to the axis of body 12, while being short enough to not completely obstruct the forward aperture 48 of body 12, to provide an obstructing wall for the needle point.

Figure 9:
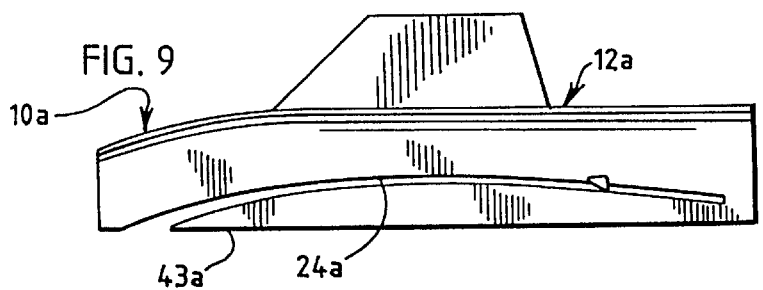
FIG. 9 is an elevational view of a modified version of the sheath of this invention.

Referring to FIG. 9, a protector sheath 10a is shown having a body 12a which may be of a design similar to that of the previous embodiments. In this particular embodiment, slots 24a on both sides of the side walls curve downwardly to pass through the lower edge 43a of body 12a, rather than passing through the end thereof as in the previous embodiments. Beyond that, the construction and use of protector sheath 10a can be similar or identical to the construction and use of the previous embodiments.

Referring to FIGS. 10 through 12 another embodiment of the protector sheath 10b is shown, being similar in structure and function to the embodiment of FIGS. 1 through 8 except as otherwise disclosed herein.

Body 12b is of U-shaped configuration as shown in FIG. 12, defining open bottom aperture 22b as before. Slots 24b are defined in each sidewall, while anchor 36b is also provided as before.

In this embodiment, locking detents 25b are an integral part of the remainder of sheath 12b, but in this embodiment, the locking detents do not project outwardly to the side, but rather project into each slot 24b in such a manner that a retracting wing of a needle can cause deflection to pass through locking detents 25b to be permanently secured in distal slot section 50 to lock the needle therein. It can be seen in this embodiment that needle tip retaining wall 46b does occupy an acute angle to the longitudinal axis in a manner previously discussed with respect to an earlier embodiment.

Detents 34b are used in a manner similar to the corresponding detents of the previous embodiments to releasably retain the needle hub 30 or the tubing attached thereto within the U-shaped protector sheath.

Also, the needle protector sheath 10b carries a pair of spaced gripping flanges 52 instead of a single gripping member as in previous embodiments, the gripping flanges 52 being positioned adjacent the proximal end of the sheath. This better facilitates the gripping of the sheath, which is rather small. A single, central gripping member would have to be unduly large relative to the typically fairly small sheath of this invention. Gripping members 52 facilitate gripping of the sheath without the need for an oversized, single gripping member which would resemble a huge dorsal fin.

Referring to FIGS. 13 through 18, sliding needle protector sheath 60 is shown as a single molded piece comprising a body 62 having a top wall 64, a pair of sidewalls 66, a bottom wall 67, and open ends as shown in FIGS. 16 and 18. Body 62 is shown to be of rectangular shape, defining an inner bore 69 for receiving a winged medical needle.

A slot 70 is defined in each of sidewalls 66, with each slot being of substantially identical shape and positioning to the other slot in the other sidewall 66. It can be seen that each slot 70 is open to the forward end 68 of body 62 particularly, intersecting the forward end 68. Each slot 70 defines upper and lower surfaces 72, 74. Most of the pair of lower slot surfaces 74 of the respective slots 70 are shown to extend straight and at an acute angle to longitudinal axis 76 of body 62, to encounter the forward body end 68 at a position that is substantially maximally spaced from top wall 64; i.e., the distance between bottom wall 67 and lower slot surface 74 at end 68 is preferably a substantial practical minimum in light of the particular engineering and economic considerations for manufacture of the specific sheath 60. Typically, the spacing between surface 74 and the bottom surface of bottom wall 67 will be no more than about 3 millimeters at end 68, preferably no more than about 1 millimeter.

The forward end portion of the upper slot surfaces 72 of the respective slots 70 can be seen to diverge from the forwardly positioned lower slot surfaces 74, to define a pair of wide slot portions 76 at forward body end 68. The respective portions 76 of slots 70 taper inwardly as the slot portions extend rearwardly from forward end 68, to communicate with the remaining portions 78 of slots 70. It can be seen that remaining portions 78 of slots 70 comprise the major portions of the respective slots 70, and in this embodiment are substantially straight along most of their length.

A wing-catching slot recess 80 receives and retains the respective needle wings when protector sheath 60 is advanced into needle-enclosing position. Slot recess 80 may be shaped to receive the desired needle wings, and to effectively permanently hold them in retained relation so that the sheath is locked in place around the needle in a manner similar to that of the prior art.

Thus, as sheath 60 is advanced along a set tube to effectively "swallow" a winged needle which is emplaced in a patient, the forward end 68 of bottom wall 67 can easily slide underneath the emplaced needle hub without causing the patient pain. At the same time, the wide, tapered slot portion 76 effectively facilitates the capture of the wings, to guide them to the straight portion 78 of each slot 70 as sheath 60 is advanced. The major portion of slot 70 occupies an acute angle to axis 77 to approximate the orientation of the needle in the patient, so that the needle is not bent or twisted as sheath 60 is advanced.

Anchor member 82 is carried as an extension of top wall 64, extending forwardly of sheath body 62, as shown, and used as described in U.S. Pat. No. 5,112,311. In this embodiment anchor 82 comprises a flat, substantially sheetlike extension of top wall 64, separated therefrom by a junction line 86 which defines a line of bending weakness, produced by the presence of a transverse groove extending partway through the plastic wall to create a hinge effect.

Also, anchor member 82 defines an outer end portion 88 which bends away from the patient in position of use, bending also away from bottom wall 67, as shown in FIG. 15. Thus, anchor 82 is rather of the shape of the front end of a ski, with curved end 88 functioning in the manner of a ski to pass over bandages of varying thickness and the like as the sheath 60 is advanced toward the needle while emplaced in the patient. Projections 89 facilitate manual retention while the anchor is being pressed against the patient and the needle being withdrawn. Junction line 86 facilitates the downward bending of anchor member 82 as it is pressed against the patient.

Thus, one may manually and easily press anchor 82 against the patient's skin and intervening bandages to retain protector sheath 60 as the needle is being withdrawn from the skin of the patient. The wings of the needle hub are captured by and move rearwardly along slots 78 until they enter slot portions 80, where they are locked in place. In this position, the needle is enclosed within the body 62 of the sheath, safely away from the risk of inflicting harm.

The rectangular cross-section of this embodiment permits the needle sheath to stand up easily on a surface, while at the same time the needle is completely enclosed within sides of the body 62 after the sheath has been advanced around the needle.

The above has been offered for illustrative purposes only, and is not intended to limit the scope of the invention of this application, which is as defined in the claims below.

That which is claimed is:

1. A medical needle protector sheath which comprises a body having a top wall, sidewalls, and at least partially open ends; a slot formed in each sidewall to receive a needle hub wing extending through each of said slots; and an elongated anchor member extending forwardly from said body to be manually pressed to retain said protector sheath in a position of use as a needle is being withdrawn from the skin of a patient, said anchor member having a straight, major portion that extends in a plane substantially parallel to the sheath longitudinal axis, said anchor member also having an outer end portion that bends away from said longitudinal axis and the patient in said position of use outwardly in an arc to facilitate passage over bandages as said sheath is advanced toward a needle to enclose said needle, said anchor member comprising a substantially flat, sheet-like extension of said top wall.

2. The protector sheath of claim 1 in which a major portion of each of said slots defines an acute angle to said longitudinal axis.

3. The protector sheath of claim 2 in which said major portions of each of said slots are straight.

4. The protector sheath of claim 1 in which said body is of rectangular cross section.

5. The protector sheath of claim 1 in which said anchor member joins said top wall at a junction line which is defined by a line of bending weakness.

6. The protector sheath of claim 1 in which said body is tapered by about 0.2° to 5° to define a forward end of said body that is of less cross section and dimension than a rear end of said body.

7. A tubular blood set which comprises flexible tubing and a medical needle carried on the end thereof, which tubular blood set carries the needle protector sheath of claim 1.

8. A needle protector sheath which comprises a body having a rear end, a top wall, sidewalls, and at least partially open ends; a slot formed at each sidewall to slidingly receive a needle wing extending through each of said slots, said slots extending generally longitudinally, said slots each defining connected forward and rear portions, said slot forward portions each sloping toward said top wall as they extend towards said rear end, and said slot rear portions each sloping away from said top wall as they extend toward said rear end.

9. The needle protector sheath of claim 8 in which said rear portions of said slot are positioned to tip the point of a needle and hub having wings carried in said rear slot portions toward said top wall.

10. The needle protector sheath of claim 9 having a longitudinal axis, and in which the forward portions of said slots sloping toward said top wall are positioned at an acute angle to the sheath longitudinal axis such that a winged needle having its wings positioned within said forward portion of the slots is not bent or twisted as the sheath and needle are brought together in use on a patient.

11. The protector sheath of claim 8 further having an anchor member which comprises a substantially flat, sheet-like extension of the top wall.

12. The protector sheath of claim 11 in which said anchor member joins said top wall at a junction line which is defined by a line of bending weakness.

13. The protector sheath of claim 8 having a longitudinal axis, and in which said slots extend through a forward end of said body, said slots each defining upper and lower surfaces, forward end portions of the lower slot surfaces extending at an acute angle to the longitudinal axis to intersect said forward body at a portion that is substantially maximally spaced from said top wall, and forward end portions of said upper slot surfaces diverging from the lower slot surfaces toward said top wall to define wide slot portions at said forward body end that taper inwardly toward each other and communicate with remaining portions of said slots.

14. The protector sheath of claim 13 which carries a bottom wall connected to the side walls, the forward end portion of said lower slot surfaces merging with the inner surface of said bottom wall adjacent to the forward end of said body.

15. The protector sheath of claim 8 in which said body is of rectangular cross-section.

16. A tubular blood set which comprises flexible tubing and a medical needle carried on the end thereof, which tubular blood set carries the needle protector sheath of claim 8.

17. A needle protector sheath which comprises a body having a rear end, a top wall, side walls, and at least partially open ends; a slot formed at each side wall to sealingly receive a needle wing extending through each of said slots, said slots extending generally longitudinally, said slots each defining connected forward and rear portions, said slot forward portions each sloping toward said top wall as they extend toward said rear end, and said slot rear portions each sloping away from said top wall as they extend toward said rear end, said body being of rectangular cross section, said protector sheath having a longitudinal axis, and in which said slots extend through a forward end of said body, said slots each defining upper and lower surfaces, forward end portions of the lower slot surfaces extending at an acute angle to the longitudinal axis to intersect said forward body at a portion that is substantially maximally spaced from said top wall, and forward end portions of said upper slot surfaces diverging from the lower slot surfaces toward the top wall to define wide slot portions at said forward body end that taper inwardly toward each other and communicate with remaining portions of said slots.

18. The needle protector sheath of claim 17 having a longitudinal axis, and in which the forward portions of said slots sloping toward said top wall are positioned at an acute angle to the sheath longitudinal axis such that a winged needle having its wings positioned within said forward portion of the slots is not bent or twisted as the sheath and needle are brought together in use on a patient.

19. The needle protector sheath of claim 18 in which said rear portions of said slot are positioned to tip the point of a needle and hub having wings carried in said rear slot portions toward said top wall.

20. The needle protector sheath of claim 19 further having an anchor member which comprises a substantially flat, sheet-like extension of the top wall.

21. The protector sheath of claim 17 further having an anchor member which comprises a substantially flat, sheet-like extension of the top wall.

22. The protector sheath of claim 21 which carries a bottom wall connected to the side walls, the forward end portion of said lower slot surfaces merging with the inner surface of said bottom wall adjacent to the forward end of said body.

23. The protector sheath of claim 17 which carries a bottom wall connected to the side walls, the forward end portion of said lower slot surfaces merging with the inner surface of said bottom wall adjacent to the forward end of said body.

24. A tubular blood set which comprises flexible tubing and a medical needle carried on the end thereof, which tubular blood set carries the needle protector sheath of claim 17.

* * * * *